US00PP16258P2

(12) United States Plant Patent
Zaiger et al.

(10) Patent No.: US PP16,258 P2
(45) Date of Patent: Feb. 14, 2006

(54) NECTARINE TREE NAMED: 'SAUZEE KING'

(50) Latin Name: *Prunus persica var. nucipersica*
Varietal Denomination: Sauzee King

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 113 days.

(21) Appl. No.: 10/989,818

(22) Filed: Nov. 17, 2004

(51) Int. Cl.
*A01H 5/00* (2006.01)

(52) U.S. Cl. ..... Plt./188
(58) Field of Classification Search ..... Plt./188
See application file for complete search history.

*Primary Examiner*—Anne Marie Grundberg

(57) ABSTRACT

A new and distinct variety of nectarine tree (*Prunus persica* var. *nucipersica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular production of fruit.
2. Fruit with very good eating quality, mild, sweet, sub-acid flavor.
3. Early maturity of peento type fruit.
4. Vigorous and upright growth of tree.
5. Fruit with an attractive red skin color.
6. Fruit with firm white flesh, good handling and shipping quality.

1 Drawing Sheet

Botanical classification: *Prunus persica* var. *nucipersica*.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of nectarine tree was originated and asexually reproduced by us in our experimental orchard located near Modesto, Stanislaus County, Calif.

Prior Varieties

Among the existing varieties of nectarine and peach trees, which are known to us, and mentioned herein, 'Honey Kist' Nectarine (U.S. Plant Pat. No. 9,333), 'Honey Blaze' Nectarine (U.S. Plant Pat. No. 10,250) and 'Saturn' peento Peach (U.S. Plant Pat. No. 2,123).

STATEMENT REGARDING FEDERALLY SPONSORED RESEARCH AND DEVELOPMENT

Not applicable.

Origin of the Variety

The new and distinct nectarine tree (*Prunus persica* var. *nucipersica*) was originated by us in our experimental orchard from seed of a first generation cross between 'Honey Kist' Nectarine (U.S. Plant Pat. No. 9,333) crossed with the proprietary seedling with field identification number 55ZA19. The parental parent (55ZA19) originated from a cross between 'Honey Blaze' Nectarine (U.S. Plant Pat. No. 10,250) and a peento peach of unknown parentage. We planted and grew a large number of seedlings, on their own root sytem, from this first generation cross and under careful observation we recognized the desirable peento fruit characteristics of the present nectarine variety and selected it for asexual propagation and commercialization.

Asexual Reproduction of the Variety

Asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of nectarine tree is of large size, vigorous, upright growth and a productive, regular bearer of medium size, white flesh fruit with very good flavor and eating quality. The fruit is further characterized by being peento shape, having firm flesh that is moderately juicy, with a mild, sweet, sub-acid flavor and having an attractive red skin color. In comparison to its maternal parent 'Honey Kist' Nectarine (U.S. Plant Pat. No. 9,333), the fruit of the new variety is white flesh compared to yellow, is peento shape compared to globose and is approximately 8 days earlier in maturity.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, its flowers, foliage and fruit, as based on observations of a 5 year old specimen grown near Modesto, Calif., with color in accordance with Munsell Book of Color.

Tree:

*Size.*—Large, pruned to 3 to 3.5 meters in height for economical harvesting of fruit.

*Vigor.*—Vigorous, growth of 1.5 to 2 meters the first growing season. Varies with type of soil, fertility and cultural practices.

*Branching habit.*—Upright, usually pruned to vase shape.

*Productivity.*—Productive, usually thinning of fruit necessary to develop desired marketable size. Fruit set varies with climatic conditions during bloom period.

*Bearer.*—Regular. Has had heavy production 3 consecutive years. No alternate bearing observed.

*Fertility.*—Self fertile.

*Density.*—Medium dense, usually pruned to vase shape by removing center branches and foliage to increase sunlight and air movement throughout the tree which enhances fruit color and keeps fruit wood healthy.

*Hardiness.*—Hardy in all stone fruit growing areas of California.

Trunk:

*Size.*—Medium. Average circumference 40.9 cm at 2.60 cm above ground level on a 5 year old tree.

*Stocky.*—Medium stocky.

*Texture.*—Medium rough, increases with age of tree.

*Color.*—Varies from 10YR 5/4 to 2.5Y 6/2.

Branches:

*Size.*—Medium. Average circumference 16.4 cm at 1 meter above ground.

*Surface texture.*—New growth relatively smooth. Mature growth medium rough.

*Lenticels.*—Average number 29 in a 25.8 square cm area. Medium. Average length 2.7 mm. Average width 1.4 mm. Color varies from 5YR 4/4 to 5YR 4/6.

*Color.*—New growth varies from 5GY 6/6 to 5YR 4/4. Mature growth varies from 10YR 6/8 to 10YR 5/8. Varies with age of growth.

Leaves:

*Size.*—Large. Average length 138.2 mm. Average width 41.2 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slight indentations over midrib and leaf veins. Lower surface relatively smooth, small ridges created by midrib and pinnate venation. Both surface glabrous.

*Petiole.*—Medium. Average length 8.9 mm. Average width 1.4 mm. Color varies from 5GY 6/6 to 5GY 6/8. Longitudinally grooved. Surface — glabrous.

*Glands.*—Reniform. Medium to large. Average length 1.1 mm. Average diameter 0.8 mm. Average number 3, varies from 1 to 4. Located primarily on base of leaf blade and upper portion of petiole. Color varies from 5GY 6/6 to 5GY 5/6.

*Color.*—Upper surface varies from 5GY 3/6 to 7.5GY 3/4. Lower surface varies from 5GY 4/4 to 7.5GY 4/4. Midvein color varies from 2.5GY 8/6 to 5GY 7/8.

Flower buds

*Size.*—Medium to large. Average length 16.7 mm. Average diameter 10.4 mm.

*Hardiness.*—Hardy in all stone fruit growing areas of California.

*Form.*—Conical, becoming elongated before opening.

*Pedicel.*—Medium. Average length 4.4 mm. Average width 1.0 mm. Color varies from 2.5GY 6/6 to 5GY 8/6.

*Color.*—Varies from 7.5RP 6/2 5RP 7/8. Varies with age of flower bud.

Flowers:

*Size.*—Large, showy. Average height 18.5 mm. Average diameter 40.3 mm.

*Petals.*—Number — normally 5, alternately arranged to sepals. Orbicular. Large. Average length 20.8 mm. Average width 22.3 mm. Margin — sinuate. Color varies from 5RP 8/6 to 5RP 7/8.

*Sepals.*—Number — 5, alternately arranged to petals. Triangular, apex rounded. Margin, entire. Large. Average length 6.3 mm. Average width 5.4 mm. Upper surface glabrous, lower surface pubescent. Color — upper surface varies from 5GY 5/4 to 5GY 5/6. Lower surface varies from 5R 3/4 to 5R 2/6.

*Stamens.*—Average number per flower 41. Average filament length 15.1 mm. Filament color varies from N 9.5/ to 5RP 7/6 as flower ages. Anther color varies from 7.5R 4/12 to 2.5Y 8.5/6.

*Pollen.*—Self fertile. Color varies from 2.5Y 8/12 to 2.5Y 7/10.

*Pistil.*—Number — usually one, varies from 1 to 2. Surface glabrous. Average length 16.4 mm. Stigma positioned an average of 1.6 mm below anthers. Color varies from 10Y 8/6 to 2.5GY to 9/6.

*Fragrance.*—Slight aroma.

*Blooming period.*—Date of First Bloom Feb. 29, 2004. Date of Petal Fall Mar. 9, 2004, varies slightly with climatic conditions.

*Color.*—Varies from 5RP 8/6 to 7.5RP 9/2. Fades as flower ages.

*Number of flowers per flower bud.*—One.

*Pedicel.*—Size — medium. Average length 4.8 mm. Average width 1.1 mm. Color varies from 2.5GY 6/8 to 5GY 6/8.

Fruit:

*Maturity when described.*—Firm ripe.

*Date of first picking.*—Jun. 4, 2004.

*Date of last picking.*—Jun. 10, 2004, varies slightly with climatic conditions.

*Size.*—Medium. Average diameter axially 38.5 mm. Average transversely in suture plane 64.0 mm. Average weight 105.1 grams, varies slightly with fertility of the soil, amount of thinning and climatic conditions.

*Form.*—Peento, donut shape.
*Suture.*—Shallow, extends from base to apex.
*Ventral surface.*—Intended, slightly lipped.
*Apex.*—Retuse, some fruit with slight apexial scarring with skin cracking.
*Base.*—Retuse.
*Cavity.*—Rounded to slightly elongated in suture plane. Average depth 2.4 mm. Average diameter 14.9 mm.

Stem:
*Size.*—Small. Average length 6.6 mm. Average diameter 2.9 mm.
*Color.*—Varies from 2.5GY 6/8 to 5GY 5/8.

Flesh:
*Ripens.*—Evenly.
*Texture.*—Firm, meaty.
*Fibers.*—Few, small, tender.
*Firmness.*—Firm, firmer than the flesh of 'Saturn' Peento Peach (U.S. Plant Pat. No. 5,123).
*Aroma.*—Moderate.
*Amydgalin.*—Undetected.
*Eating quality.*—Very good.
*Flavor.*—Very good, mild, sweet, sub-acid.
*Juice.*—Moderate, enhances flavor.
*Brix.*—Average of 14.0°, varies slightly with amount of fruit per tree and climatic conditions.
*Color.*—Varies from 7.5Y 9/4 to 7.5Y 8/6. Pit cavity varies from 2.5Y 7/6 to 5Y 7/6.

Skin:
*Thickness.*—Medium.
*Surface.*—Smooth.
*Down.*—Wanting.
*Tendency to crack.*—Slight, primarily near apex.
*Color.*—Ground color yellow, varies from 5Y 9/4 to 5Y 8/6. Overspread with 5R 3/10 to 7.5R 3/8.
*Tenacity.*—Tenacious to flesh.
*Astringency.*—None.

Stone:
*Type.*—Clingstone.
*Size.*—Medium to large. Average length 20.7 mm. Average width 28.3 mm. Average thickness 25.8 mm.
*Form.*—Peento shape, resembles shape of fruit.
*Base.*—Flat.
*Apex.*—Rounded.
*Surface.*—Pitted throughout, pits vary from round to elongated.
*Sides.*—Unequal, one side extending outward further form suture plane.
*Ridges.*—Small, narrow, ridges extending from base toward apex.
*Tendency to split.*—None.
*Color.*—Varies from 7.5YR 7/8 to 7.5YR 6/8.

Kernal:
*Size.*—Medium. Average length 10.7 mm. Average width 9.8 mm. Average thickness 7.7 mm.
*Form.*—Ovate, more rounded than most nectarine kernals.
*Viability.*—Non-viable, incomplete embryo.
*Skin color.*—5Y 8/4 when dry.

Use: Dessert. Market, local and long distant.

Keeping quality: Good, held firm in cold storage 2 weeks at 38° to 42° F. without internal breakdown or appreciable loss of flavor.

Shipping quality: Good, minimal skin scarring or bruising of flesh during handling and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct nectarine tree (*Prunus persica* var. *nucipersica*) substantially as illustrated and described, characterized by its large size, vigorous, upright growth, and a productive, regular bearer of medium, firm, white flesh, peento type, clingstone fruit with very good flavor and eating quality. The fruit is further characterized by having an attactive red skin color and, in comparison to its maternal parent 'Honey Kist' Nectarine (U.S. Plant Pat. No. 9,333), the fruit of the new variety is white fleshed, compared to yellow, has peento fruit shape compared to globose and is approximately 8 days earlier in maturity.

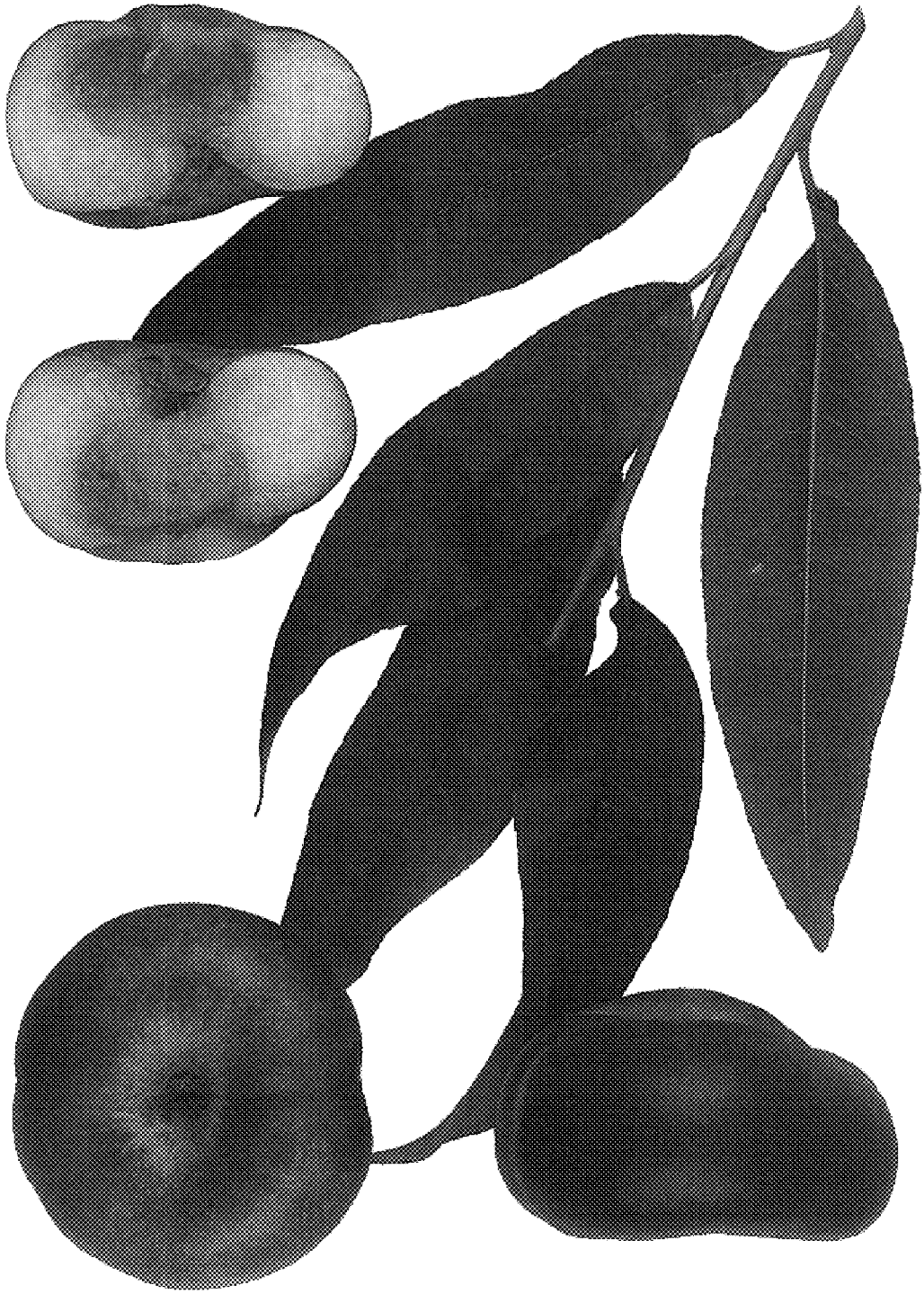

* * * * *